United States Patent
Karabacak et al.

(10) Patent No.: US 11,231,350 B2
(45) Date of Patent: Jan. 25, 2022

(54) PROBE FOR DETERMINING SOIL PROPERTIES

(71) Applicant: Fugro Technology B.V., Leidschendam (NL)

(72) Inventors: Devrez Mehmet Karabacak, Leidschendam (NL); Peter Looijen, Leidschendam (NL); Bastiaan Meulblok, Leidschendam (NL); Eric Meijer, Leidschendam (NL)

(73) Assignee: FUGRO TECHNOLOGY B.V.

( * ) Notice: Subject to any disclaimer, the term of this patent is extended or adjusted under 35 U.S.C. 154(b) by 314 days.

(21) Appl. No.: 16/342,285

(22) PCT Filed: Oct. 20, 2017

(86) PCT No.: PCT/NL2017/050688
§ 371 (c)(1),
(2) Date: Apr. 16, 2019

(87) PCT Pub. No.: WO2018/074928
PCT Pub. Date: Apr. 26, 2018

(65) Prior Publication Data
US 2019/0234848 A1    Aug. 1, 2019

(30) Foreign Application Priority Data

Oct. 20, 2016 (NL) .................................. 2017647

(51) Int. Cl.
*G01N 3/06* (2006.01)
*E02D 1/00* (2006.01)
(Continued)

(52) U.S. Cl.
CPC .............. *G01N 3/068* (2013.01); *E02D 1/00* (2013.01); *G01N 3/48* (2013.01); *G01N 33/24* (2013.01)

(58) Field of Classification Search
CPC ....... G01L 11/025; G01L 1/246; G01L 7/065; G01L 9/0076; E21B 47/06; E21B 47/09;
(Continued)

(56) References Cited

U.S. PATENT DOCUMENTS 5,902,939 A * 5/1999 Ballard ................. E21B 49/081
73/863.12
6,278,811 B1 * 8/2001 Hay ...................... G01L 11/025
385/13
(Continued)

FOREIGN PATENT DOCUMENTS

EP       2282006 A1   2/2011
WO   2014129704 A1   8/2014
(Continued)

OTHER PUBLICATIONS

International Search Report and Written Opinion; PCT Application No. PCT/NL2017/050688; dated Dec. 12, 2017.

*Primary Examiner* — Nimeshkumar D Patel
*Assistant Examiner* — Gedeon M Kidanu
(74) *Attorney, Agent, or Firm* — Polsinelli PC (57) ABSTRACT

The invention relates to a probe arranged for subsurface penetration of a soil for measuring properties of the soil. The probe comprising a probe body and at least one fiber optical sensor. The at least one fiber optical sensor is arranged for measuring at least one of a cone resistance, sleeve friction, pore water pressure or inclination.

19 Claims, 5 Drawing Sheets

(51) Int. Cl.
*G01N 3/48* (2006.01)
*G01N 33/24* (2006.01)

(58) Field of Classification Search
CPC ... E21B 47/135; G01B 11/18; G01D 5/35316; G01H 9/004; G01K 11/3206; G01K 2011/322; G01N 2201/088; G01N 2201/0886
See application file for complete search history.

(56) References Cited

U.S. PATENT DOCUMENTS

| | | | | |
|---|---|---|---|---|
| 6,563,970 | B1* | 5/2003 | Bohnert | G01L 9/0007 385/13 |
| 8,444,937 | B2* | 5/2013 | Tuli | G01V 9/00 422/535 |
| 8,676,008 | B2* | 3/2014 | Grosso | G01V 1/186 385/37 |
| 9,360,643 | B2* | 6/2016 | Rinzler | G02B 6/3813 |
| 2006/0139626 | A1* | 6/2006 | Childers | G01C 9/06 356/138 |
| 2008/0317401 | A1* | 12/2008 | Huang | G01L 11/025 385/13 |
| 2010/0219334 | A1* | 9/2010 | Legrand | E21B 47/103 250/256 |
| 2010/0257920 | A1* | 10/2010 | Lee | E02D 1/022 73/84 |
| 2014/0123764 | A1* | 5/2014 | Abtahi | G01L 7/065 73/705 |
| 2014/0326078 | A1* | 11/2014 | Arkwright | G01K 11/3206 73/862.624 |
| 2015/0177411 | A1* | 6/2015 | Childers | G02B 6/02076 250/269.1 |
| 2015/0204743 | A1* | 7/2015 | Nieuwland | G01D 5/268 73/705 |
| 2016/0116369 | A1* | 4/2016 | Barry | G01K 11/3206 356/73.1 |
| 2016/0223710 | A1* | 8/2016 | Barry | G01D 5/35316 |
| 2017/0370064 | A1* | 12/2017 | Morgan | G01J 3/0208 |

FOREIGN PATENT DOCUMENTS

| WO | 2018074928 A1 | 4/2018 |
|---|---|---|
| WO | 2018074928 A8 | 4/2018 |

* cited by examiner

FIG. 5 ns. In optical fiber sensors an optical fiber is used as a sensing element. The optical fiber can be lit (e.g. by a laser), and a change in the fiber due to an external cause (dependent on the type of sensor) results in a measurable change in the optical signal transmitted by or received from the sensor.

PROBE FOR DETERMINING SOIL PROPERTIES

CROSS-REFERENCE TO RELATED APPLICATIONS

This application is a national stage application of International Application No. PCT/NL2017/050688, which was filed on Oct. 20, 2017, which claims priority to Netherlands Application Number 2017647 filed on Oct. 20, 2016, of which is incorporated by reference in its entirety.

FIELD OF THE INVENTION

The invention relates to a probe, a method and a system for determining soil properties.

BACKGROUND TO THE INVENTION

A cone penetration test (CPT) is a geotechnical investigation method for determining soil and groundwater characteristics, wherein a penetrometer probe is pushed into the soil for measuring. Typical parameters measured by a probe are cone tip resistance, sleeve friction and pore-water pressure. Usually, a plurality of electric strain gauges are used in the probe. Other electric sensors are also possible. Since the probe is designed for insertion into the ground, the size of the sensors in the probe needs to be limited. Advantageously, miniaturization of the sensors can result in a reduction of the overall dimensions of the penetrometer. However, achieving a desired size reduction often comes at the cost of sensitivity of the sensor, and this trade-off is usually not desired. Moreover, sensitivity and size are not the only characteristics that are of interest. For example, the electric sensors may require many wires which need to be guided to the probe. Furthermore, the electric sensors are also sensitive for humidity and temperature changes.

SUMMARY OF THE INVENTION

It is an objective to provide an improved probe usable for cone penetration tests.

Thereto, according to an aspect is provided a probe arranged for subsurface penetration of a soil for measuring properties of the soil comprising a probe body and at least one fiber optical sensor. The at least one fiber optical sensor is arranged for measuring at least one of a cone resistance, sleeve friction, pore water pressure or inclination.

Fiber optic sensing has several advantages that can provide benefits in many operations of large scale data acquisition. Fiber optic sensing allows to form passive (electrical power free) sensors eliminating the need to provide power to the sensing point. Fiber optic sensing allows multiplexing of sensor signals, which allows for formation of chains of sensors on single fibers without needing expensive and heavy cabling. Fiber optic sensing provides the ability to transduce various physical effects by recording various fiber optic sensors using a single generic common read-out platform and essentially sharing the optoelectronic system and computation platform to form a low cost large scale sensing system. Fiber optic sensing provides remote measurement capability owing to the fact that long distance low-loss, interference free, high bandwidth signal transmission can be achieved with a low cost communication fiber. Fiber optic sensing is compatible with harsh environments, especially by using coated glass fibers, which can e.g. withstand 300° C. and/or have high chemical resistance to external substances.

Optionally, the at least one fiber optical sensor includes a Fiber Bragg Grating, FBG. An FBG comprises a fiber having a core including therein, over a certain distance, a periodic variation of the refractive index. This periodic variation forms a wavelength-specific dielectric mirror, wherein light in a specific (narrow) range around and including a certain wavelength is reflected. The wavelength reflected is determined by the periodicity of the refractive index of the core. The FBG is based on the principle that a difference in strain of the optical fiber causes the geometric periodicity of the variations to change. This results in a change of the reflected wavelength, such change can be detected (e.g. by spectral analysis, or using an interferometer). FBGs are applied in many applications for measuring a wide range of parameters and characteristics, including static and dynamic parameters.

Optionally, the at least one fiber optical sensor includes at least one first fiber optic portion including at least one Fiber Bragg Grating, FBG, for measuring a force on an external surface of the probe. The external surface can e.g. be a tip or a sleeve.

Optionally, the at least one fiber optical sensor includes a pair of Fiber Bragg Gratings including a first FBG of the pair and a second FBG of the pair. The pair can be arranged such that in the first and second FBG a response to a temperature change is similar, e.g. having the same sign, and optionally magnitude. The pair can be arranged such that in the first and second FBG a response to a temperature change is identical. The pair can be arranged such in the first and second FBG a response to the force is different. The pair can be arranged such in the first and second FBG a response to the force is of opposite sign, and e.g. equal or, at least, proportional magnitude. Hence, a response due to a temperature change can easily be distinguished from a response due to force, e.g. by addition or subtraction of the signals of the first and second FBG of the pair (or a signal proportional to them). The response to temperature change can e.g. be due to thermal elongation/contraction of the probe.

Optionally, the at least one fiber optical sensor includes a pair of Fiber Bragg Gratings arranged such that the force simultaneously causes elongation of a first FBG of the pair and shortening of a second FBG of the pair. The pair of FBG can be arranged such that the force simultaneously causes an increase of the tension of a first FBG of the pair and decrease of the tension of a second FBG of the pair. Hence, the force to be determined simultaneously causes opposite effects in the first and second FBGs of the pair. Hence, a response due to temperature change can easily be distinguished from a response due to force. Also, since force is measured by two FBGs simultaneously, accuracy can be improved.

Optionally, the first FBG of the pair and the second FBG of the pair are included in series in a single fiber optic portion. Optionally, the first and second FBGs both extend in an axial direction of the probe body.

Optionally, the probe includes a sleeve for transferring the force from the external surface of the probe onto the first and second FBG of the pair.

Optionally, the sleeve is connected to the single fiber optic portion between the first and second FBGs of the pair. Hence, the sleeve can easily actuate the first and second FBGs of the pair simultaneously.

Optionally, the single fiber optic portion is connected to the probe body at attachments such that the first and second FBGs of the pair are positioned between the attachments. The first and second FBGs of the pair can e.g. extend between the attachments along a straight line. The force to be determined can be applied at a center attachment on the single fiber optic portion between the first and second FBGs of the pair.

Optionally, the probe body includes a first measurement section and at least one first optic fiber portion, e.g. at least two first optic fiber portions, extending along the first measurement section in an axial direction of the probe body, for measuring cone resistance. The first measurement section can include a first sleeve, connecting a cone tip to a first fiber optic portion including the pair of FBGs. The first measurement section can be a flexible section allowing a cone tip to move relative to the remainder of the probe body. The movement of the cone tip can be sensed as strain in the first optic fiber portion(s). Using three first optic fiber portions, e.g. distributed along a circumference of the probe body, allows to measure unequal loads to the cone tip and resulting bends of the probe. The first optic fiber portion can be distributed uniformly along the circumference of the probe body. The first fiber portions can be aligned parallel to an axial axis of the probe body.

Optionally, the probe body includes a second measurement section and at least one second optic fiber portion, e.g. at least two second optic fiber portions, extending along the second measurement section in an axial direction of the probe body, for measuring sleeve friction. The second measurement section can include a second sleeve, connecting a friction sleeve to a second fiber optic portion including the pair of FBGs. The second measurement section can be a flexible section allowing the friction sleeve to move relative to the remainder of the probe body. The movement of the friction sleeve can be sensed as strain in the second optic fiber portion(s). Using three second optic fiber portions, e.g. distributed along a circumference of the probe body, allows to measure unequal loads to the friction sleeve. The second optic fiber portion can be distributed uniformly along the circumference of the probe body. The second fiber portions can be aligned parallel to an axial axis of the probe body.

Optionally, at least one first optic fiber portion aligns with at least one second optic fiber portion. Optionally, each first optic fiber portion aligns with a corresponding second optic fiber portion.

Optionally, at least one first optic fiber portion and at least one second optic fiber portion are part of a single optic fiber. This provides the advantage that a simple mechanical construction is obtained. Moreover, the measurements at the first and second fiber optic portions can be multiplexed in the single optic fiber. Optionally, each first optic fiber portion is part of a single optic fiber together with a corresponding second optic fiber portion. Optionally, all first optic fiber portions and all second optic fiber portions are part of one single optic fiber.

Optionally, the probe includes a pore pressure sensor including a third optic fiber portion extending between a displaceable diaphragm and a point fixed on the probe body in a closed chamber at a reference pressure. The displaceable diaphragm can be a wall of the closed chamber. The displaceable diaphragm can be exposed to the pressure of pore water, e.g. via bores in the probe. The pore pressure sensor can be positioned directly behind the cone tip.

Optionally, the probe includes a temperature sensor including a fourth optic fiber portion extending between two mounts free from mechanical strain. The fourth optic fiber portion can e.g. be mounted in a tube. Since the fourth optic fiber portion is mounted free from mechanical strain, it will only measure temperature effects.

Optionally, the third optic fiber portion and the fourth optic fiber portion are part of a single optic fiber. The fourth optic fiber portion can be positioned inside the closed chamber. The tube can be positioned inside the closed chamber.

Optionally, the probe includes a temperature reference sensor including a fifth optic fiber portion. Optionally, the probe includes three fifth optic fiber portions. The fifth optic fiber portion can extend between two mounts free from mechanical strain. The fifth optic fiber portion can be part of a single optic fiber together with at least one first optic fiber portion and at least one second optic fiber portion. The fifth optic fiber portion can be positioned in between the first and second fiber optic portions. Optionally, each first optic fiber portion is part of a single optic fiber together with a corresponding second optic fiber portion and a corresponding fifth fiber optic portion. Optionally, all first optic fiber portions, all second optic fiber portions and all fifth fiber optic portions are part of one single optic fiber.

Optionally, calibration of the temperature sensor and/or temperature reference sensor of the probe is carried out for compensating at least one of a cone resistance, sleeve friction or pore water pressure for underground temperature change during a cone penetration test. Optionally, the compensation based on the sensed temperature is carried out in real-time. Optionally, the compensation is carried out during post-processing.

Optionally, the probe including an inclination sensor including a suspended mass pivotally connected to the probe body, and at least three sixth optic fiber portions extending between the suspended mass and the probe body. The three sixth optic fiber portions allow for two-axis measurement of inclination. The three sixth optic fiber portions can be distributed, e.g. uniformly, around a perimeter of the suspended mass. Optionally, each sixth optic fiber portion is part of a single optic fiber together with a corresponding first, second, and optionally fifth, optic fiber portion. Optionally, all first optic fiber portions, all second optic fiber portions, all sixth optic fiber portions, and optionally all fifth fiber optic portions, are part of one single optic fiber.

Optionally, the suspended mass is included in a chamber filled with a liquid. This allows for damping of motion of the suspended mass and may prevent damage due to shock.

Optionally, the at least one optical fiber sensor includes an optic fiber portion anchored by anchors wherein the anchors have a thermal expansion arranged to counteract a thermal expansion of the probe body between the anchoring points of the optic fiber portion. Hence thermal expansion of the probe body can be, partially or wholly, be counteracted. Preferably, the thermal expansion of the anchors is designed to completely counteract thermal expansion of the probe body within the required operating range. Optionally, the first and/or second optic fiber portions are suspended using said anchors. Optionally, the third and/or fifth optic fiber portions are suspended using said anchors.

The one or more adjustable anchors can be used to correct a temperature effect on the FBG sensors during the penetration of the probe. Optionally, a compensation is performed during cone penetration, with a particular configuration of the present invention as disclosed, the compensation is advantageously made in real-time. In this way, a mechanical temperature compensation of a strained FBG can be obtained. By use of thermally expanding attachments, the effect of a temperature increase can be compensated. In ideal situations, the thermal sensitivity of the FBG sensors can be eliminated by reducing the pretension by well matched expansion of material with different thermal expansion than the cone body.

Optionally, the first, second, third, fourth, fifth, and/or sixth optic fiber portions include a Fiber Bragg Grating. Optionally, all optic fiber portions in the probe are merged into one single optical fiber before exiting to the connection rod.

Optionally, all sensors in the probe are fiber optic sensors. Optionally, the probe is free from electric and/or electronic sensors. Optionally, the probe is free from electronic components.

According to an aspect is provided a probing system including a probe as described above. The probing system includes a drive unit arranged for driving the probe into the soil. The probing system includes a data acquisition system arranged for sampling measurement signals from the probe. The data acquisition system can include a fiber optic interrogator arranged for carrying out interrogation of the one or more optical fiber sensors of the probe. The probing system can include a control unit. The control unit can be arranged for controlling the probe, the drive unit, and/or the data acquisition unit.

Optionally, the probe is connected to the data acquisition unit via one or more optical fibers. Optionally, the probe is connected to the data acquisition unit via a single optical fiber. Optionally, a plurality of FBGs can be split to several fibers.

The arrangement of optical fiber sensors in a probe for measuring soil properties, e.g. for cone penetration testing, can provide significant advantages with respect to the convention probe with electrical sensors. The accuracy can be improved, while reducing the size of the probe. Furthermore, it may not be required to provide multiple electrical powerlines and communication lines to the electric sensors. Moreover, optical fiber sensors are corrosion resistant and also not sensitive to electro-magnetic influences and humidity inside the probe.

According to an aspect is provided a method for determining soil properties. The method comprises pushing a probe into a soil. The probe can be a probe as described above. The method includes determining at least one of a cone resistance, sleeve friction, pore water pressure or inclination.

Additionally, regarding data acquisition rates, while the interrogator can be operated at a frequency to record all the sensors (e.g. 1 kHz), this frequency may not be necessary for the recordings by the probe optical fiber sensors. For example, recordings up to 10 Hz ca be sufficient. As such, an averaging factor (e.g. 100 in this example) can be implemented to provide better signal to noise for all of the sensors. Furthermore, a polarization control feature of the interrogator can be used for eliminate potential polarization effects in the communication fiber.

Optionally, the system is arranged on a movable unit. A movable unit can for instance be a vehicle, truck, tracktruck, stand-alone device, crawler, CPT-crawler, standard CPT-truck, CPT-minicrawler, etcetera. Depending on the terrain, area and space conditions the right choice for a movable unit can be chosen. Optionally, the system is arranged to perform in-situ measurements. The system can also be mountable on vehicles, boats, pontoons, etcetera. Different combinations are possible.

It will be appreciated that any of the aspects, features and options described in view of the probe apply equally to the described system and method, and vice versa. It will also be clear that any one or more of the above aspects, features and options can be combined.

BRIEF DESCRIPTION OF THE DRAWING

The invention will further be elucidated on the basis of exemplary embodiments which are represented in a drawing. The exemplary embodiments are given by way of non-limitative illustration. It is noted that the figures are only schematic representations of embodiments of the invention that are given by way of non-limiting example.

In the drawing.

DETAILED DESCRIPTION

Figure 1:
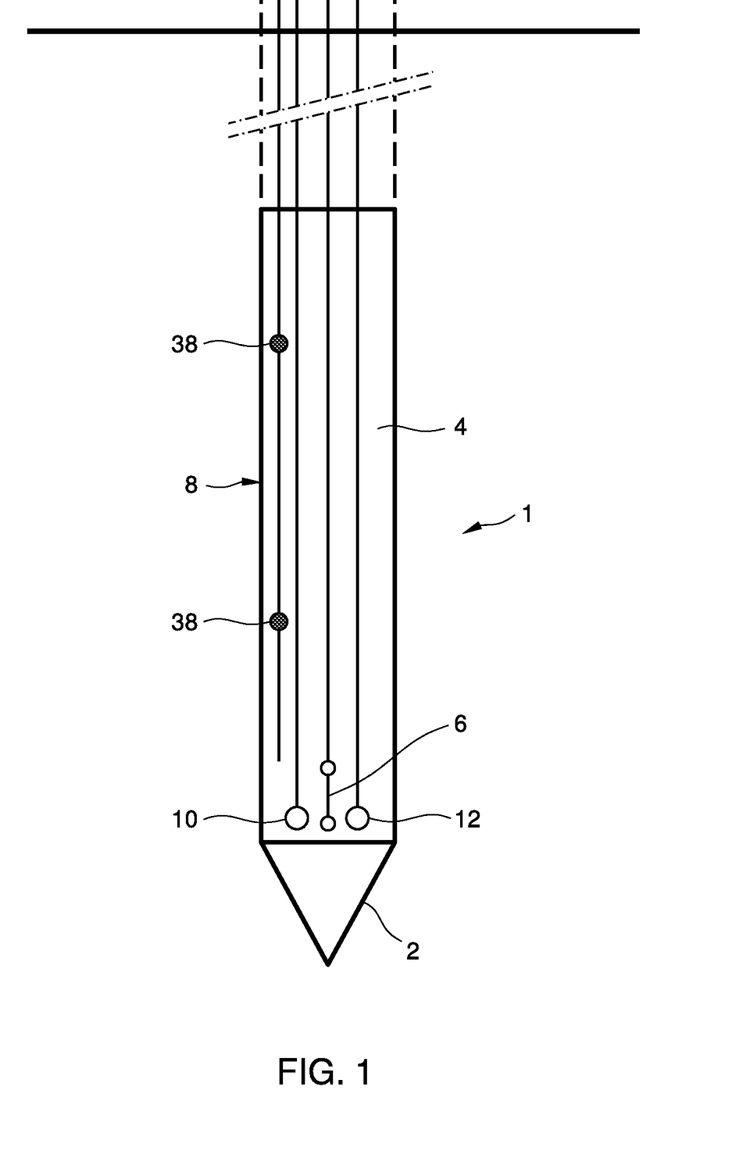
FIG. 1 shows a schematic representation of a cone penetrometer.

FIG. 1 shows a schematic representation of a cone penetrometer 1. The cone penetrometer 1 includes a cone tip 2. The penetrometer 1 includes a sleeve 4. The cone tip 2 is associated with a cone tip resistance sensor 6 for measuring cone tip resistance. The sleeve 4 is associated with a sleeve friction sensor 8 for measuring sleeve friction. The penetrometer 1 includes a pressure sensor 10 for measuring pore water pressure. The penetrometer 1 includes a temperature sensor 12 for measuring penetrometer temperature One or more of the sensors 6, 8, 10, 12 of the penetrometer 1 can be designed as fiber optic sensors. In the example of FIG. 1 all sensors 6, 8, 10, 12 are fiber optic sensors. The fiber optic sensor can be a Fiber Bragg Grating, FBG, sensor.

An FBG comprises an optic fiber having a core including therein, over a certain distance, a periodic variation of the refractive index. The periodic variation forms a wavelength-specific dielectric mirror, wherein light in a specific (narrow) range around and including a certain wavelength is reflected. The wavelength reflected is determined by the periodicity of the refractive index of the core. The FBG sensor is based on the principle that a difference in mechanical strain of the optical fiber causes the geometric periodicity of the variations to change. This results in a change of the reflected wavelength. Such wavelength change can be detected, e.g. by spectral analysis, or using an interferometer.

Although the FBG sensor measures mechanical strain, an FBG can also be used in a pressure sensor by converting an exerted exterior pressure into a variable force applied to the optical fiber including the FBG. Also, an FBG can be used in a temperature sensor by converting an exerted temperature into a variable force applied to the optical fiber including the FBG, e.g. by using thermal expansion/contraction.

Fiber optic sensing, such as Fiber Bragg Grating based sensing, is a promising measurement technique. Fiber optic sensing has several advantages that can provide benefits in many operations of large scale data acquisition. Fiber optic sensing allows to form passive (electrical power free) sensors eliminating the need to provide power to the sensing point. Fiber optic sensing allows multiplexing of sensor signals, which allows for formation of chains of sensors on single fibers without needing expensive and heavy cabling.

Fiber optic sensing provides the ability to transduce various physical effects by recording various fiber optic sensors using a single generic common read-out platform and essentially sharing the optoelectronic system and computation platform to form a low cost large scale sensing system. Fiber optic sensing provides remote measurement capability owing to the fact that long distance low-loss, interference free, high bandwidth signal transmission can be achieved with a low cost communication fiber. Fiber optic sensing is compatible with harsh environments, especially by using coated glass fibers, which can e.g. withstand 300° C. and/or have high chemical resistance to external substances.

Figure 2A:
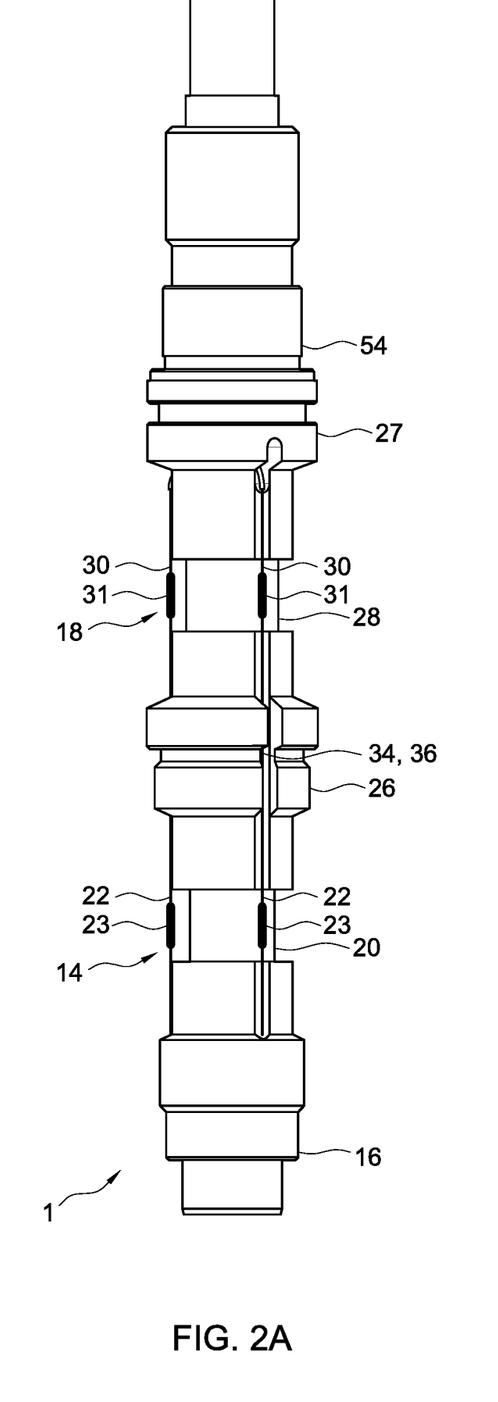
FIGS. 2A and 2B show schematic representations of an example of a cone penetrometer.
Figure 2B:
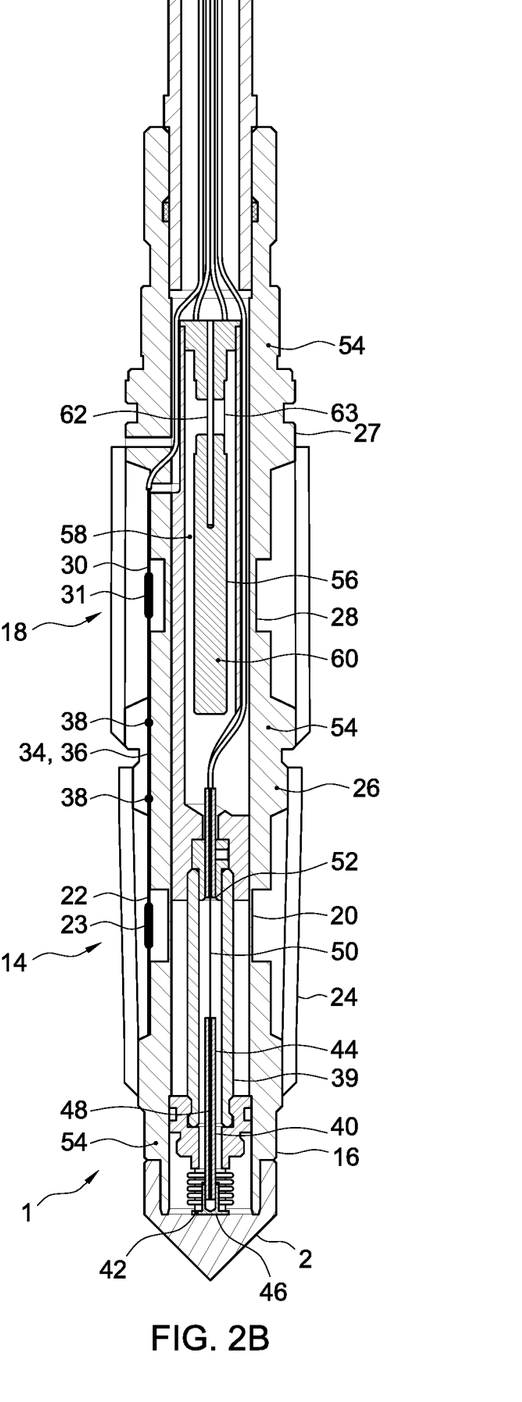

FIGS. 2A and 2B show schematic representations of an example of a cone penetrometer 1. FIG. 2A shows a side view. FIG. 2B shows a cross sectional view.

In a first section 14, cone resistance measurement can be performed. The cone tip 2 is attached to a cone tip attachment unit 16. The cone tip attachment unit 16 connects to a center unit 26 via a first flexible section 20. Here the flexible section 20 is formed by a wall thickness reduced region which will be flexible under axial load generated by the force on the tip 2. In the first section three first optic fiber portions 22 are provided, each with their own Fiber Bragg Grating 23. The three fiber portions 22 are radially distributed with 120 degree separations. Hence, the three fiber portions 22 span the flexible section 20 to measure the length change of the deformable region. In this example, the Fiber Bragg Gratings 23 of the first optic fiber portions 22 are positioned over the first flexible section 20. By performing strain measurements at three locations radially distributed, effects of unequal loads at the tip and resulting bends can be corrected in the measurements. A cover 24 protects the fiber portions 22 from mechanical damage.

In a second section 18, sleeve friction measurement can be performed. The center unit 26 is attached to a back unit 27. The center unit 26 connects to the back unit 27 via a second flexible section 28. A cover 32 is connected to the center unit 26 and acts as a sleeve to provides the sleeve friction. Here the flexible section 28 is formed by a wall thickness reduced region which will be flexible under axial load due to the combined load of cone resistance and sleeve friction. In the second section 18 three second optic fiber portions 30 are provided, each with their own Fiber Bragg Grating 31. The three fiber portions 30 are radially distributed with 120 degree separations. Hence, the three fiber portions 30 span the flexible section 28 to measure the length change of the deformable region. In this example, the Fiber Bragg Gratings 31 of the second optic fiber portions 30 are positioned over the second flexible section 28. By performing strain measurements at three locations radially distributed, effects of unequal loads at the tip and sleeve resulting bends can be corrected in the measurements. The cover 32 also protects the fiber portions 30 from mechanical damage.

Here each of the fiber portions 22 in the first section 14 is aligned with a corresponding fiber portion 30 in the second section 18. Here each fiber portion 22 and the corresponding aligned fiber portion 30 are part of a single optic fiber. The FBG of the fiber portion 22 can be tuned to a different wavelength than the FBG of the fiber portion 30. Thus FBGs of the first section and the second section can be chained onto one fiber and recorded simultaneously.

In this example, in between the first and second sections, e.g. in the non-deformed region, a temperature sensor 34 is located. Here the temperature sensor includes a length of fiber optic 36 clamped in two anchors 38. The fiber optic 36 includes a reference FBG. Relative movement of the anchors 38 due to thermal expansion/contraction causes strain in the FBG, allowing temperature measurement. The measured temperature can be used for temperature correction of the strain measurements in either of the first and second sections. While only one is considered here, the reference FBG can be also on each of the 3 fiber chains for better accuracy. The reference fiber optic(s) 36 can be part of a single fiber optic together with a fiber portion 22 of the first section 14 and a fiber portion 30 of the second section 18.

In the cone tip attachment unit 16, a pore pressure sensor 39 is provided. In this example, in the cone tip attachment unit 16, also a temperature sensor 40 is provided. Here, a combined pressure-temperature sensor is formed by use of a pressure deformable body 42 with a tube 44 connected perpendicular to the effective surface 46 under pressure, whereby inside the tube a first FBG 48 is integrated for temperature measurements and a second FBG 50 is spanned pre-tensioned from the end of the tube 44 to a fixation point 52 in the cone body 54. The strain on the second FBG 50 will be indicative of the deformation of the pressure sensing element with the temperature correction applied, as further discussed below. The part inclusive of the tube 44 and the free span fiber is sealed under a reference pressure, e.g. 1 bar, to ensure a well calibrated pressure reading.

Further, an inclinometer 56 is provided inside a hollow core 58 in the second section 18. A two-axis inclination measurement can be achieved by a suspended mass 60 attached with a pivoting rod 62 to the cone body 54 and connected with three fiber sections 63 with Bragg gratings, e.g. at equal radial spacing of 120 degrees. The hollow core 58 can be filled with a, e.g. viscous, liquid to protect the suspended mass 60 from hitting the inner walls of the hollow core 58 upon shocks.

As such, the penetrometer 1 of the example of FIG. 2 includes at least twelve FBGs: three for measuring cone resistance, three for measuring sleeve friction, three for measuring inclination, one reference FBG and two in the pressure-temperature sensor. Using these at least twelve FBGs allows measuring all the desired measurements with sufficient selectivity to potentially interfering effects.

Fiber Bragg Grating and Interrogation Specifications

The cone resistance and sleeve friction measurements are strain-based measurements and as such an equal sensitivity and accuracy will be achieved regardless of FBG fiber diameter, since strain sensitivity of FBGs is diameter independent. Similarly, the temperature sensitivity of FBGs is fiber diameter independent. However, both the pressure and tilt angle measurement concepts proposed here, are force-based measurements, as discussed in more detail below, and as such obtaining the lowest axial stiffness in the fiber is key. Therefore, thin fibers are preferred, such as 80 μm diameter fibers (or thinner) are recommended for these transducers. To maintain uniformity between FBGs in the cone, it can be considered to use the same fiber for all sensing points.

For measuring the fiber optic cone penetrometer, can include an interrogator for interrogating each of the FBGs. For offshore measurements, the interrogator can be placed on the deck of a geotechnical vessel and use a communication fiber down to the cone penetrometer. Also operation of a slip ring between the penetrometer and the interrogator introduces minimal error to the measurements. This approach can provide the advantage of removing the need for electronic acquisition unit to be in the subsea.

If additional functions of the penetrometer require an electronic control or data acquisition unit to be stationed subsea anyway, then the interrogator can also be integrated in the subsea unit if advantageous to do so.

Temperature Correction

As described above and indicated in FIG. 2, a separate, unstrained FBG 36 can be provided for correcting the temperature effects. The length of fiber 36 in FIG. 2B is between the two deforming sections of the rod. However, the accuracy to which temperature can be compensated will be largely governed by the thermal gradients between the temperature reference point and the strain measurement points, and the temperature sensitivity of the strain gauges.

Under simplest attachment scheme, the temperature sensitivity picked up by the reference FBG 36 will be largely due to the thermal expansion of the cone rod 54. This thermal expansion can introduce a cone resistance pressure equivalent error. Clearly, such error can benefit from correction and compensation. According to an option, a mechanical temperature compensation of a strained FBG is provided by use of thermally expanding attachment anchors of the FBG. The thermally expanding anchors include a material with different thermal expansion than the cone body 54. By well-matched expansion of the material of the cone body and that of the anchors, thermal sensitivity of the FBG strain sensor can be eliminated or at least reduced. Additionally, the temperature compensation FBG 36 could still be used to correct for residual temperature sensitivity.

High Fidelity Coupling of Strain to FBG

With the large loads and strain levels anticipated in the upper limits of operation range, it is important to ensure that the attachment points of the FBG are well defined, robust and rigid, to ensure lossless transmission of the strain to the optical fiber.

Temperature Sensor

For temperature measurement, a location close to the tip of the cone is proposed, e.g. just behind the pore pressure transducer. For the temperature sensor, a simple, tubed, unstrained FBG is provided here as the temperature sensor. FBGs have a very reproducible sensitivity to temperature with 10 pm/C sensitivity, and this can be leveraged to provide 0.1° C. accuracy reading of the temperature at the sensor location using the standard performance an interrogator.

Pore Pressure Gauge

Measurement of pore pressure is typically facilitated via side holes behind the conical tip of the cone. The pressure force transduction mechanisms can be based on bellows. This provides a high linear range, availability in a wide range of dimensions and rigidities, and relatively low cost high volume availability. Alternatively, a diaphragm-based transducer element can be used with sufficient rigidity but with the limitation that the system will be inherently non-linear as all membrane type transducers are. A 12 mm diameter diaphragm with 0.9 mm thickness milled out of the same cone body material (e.g. Armco 17-4 PH) has been calculated to provide sufficient rigidity while providing an FBG wavelength pressure sensitivity of approximately 11 pm/bar. The nonlinearity effect can be corrected in calibration with multiparameter fittings to yield a negligible error. Due to the limited sensitivity that can be achieved in the pressure gauge, the temperature induced error can be of considerable source of inaccuracy if not corrected effectively. Therefore, the temperature sensitivity of the pressure gauge can lowered using the same thermally expanding attachments mechanism described above. Further correction for remaining temperature effects can then be achieved in calibration constants by using the measurements from the temperature gauge 36 which is in close proximity to the pressure measurement FBG.

Inclinometer

A tilt sensor is used in the cone penetrometer to better map its path during measurements and correct for tilts in the data acquisition or analysis. Here, a two directional fiber optic tilt sensor has been provided as a suspended pendulum connected with three FBG fibers, distributed radially at 120 degree spacings. By using this sensing point layout, it is possible to ensure that temperature and axial rotational effects are all canceled out in the measurements. Within the space available in the cone, a 25 gram mass as tilt sensor has been calculated to yield approximately 14 pm/degree sensitivity allowing for a measurement resolution of about 0.1 degree.

As mentioned above, the enclosure of the tilt sensor is can be filled with a sufficiently viscous fluid to ensure the suspended mass is not damaged due to shocks during operations or handling.

Optical Interrogation, Bandwidth and Fiber Connectivity

In view of the challenges in ensuring a well-sealed fiber connection to the inside of the cone, the number feedthroughs can be minimized to one fiber. All of the above described measurement points with the twelve FBGs can be measured using a single communications fiber. For example, all twelve FBG measurements can be fitted into the 40 nm C-band of a FAZ 14 interrogator at 1 kHz scans.

Figure 3A:
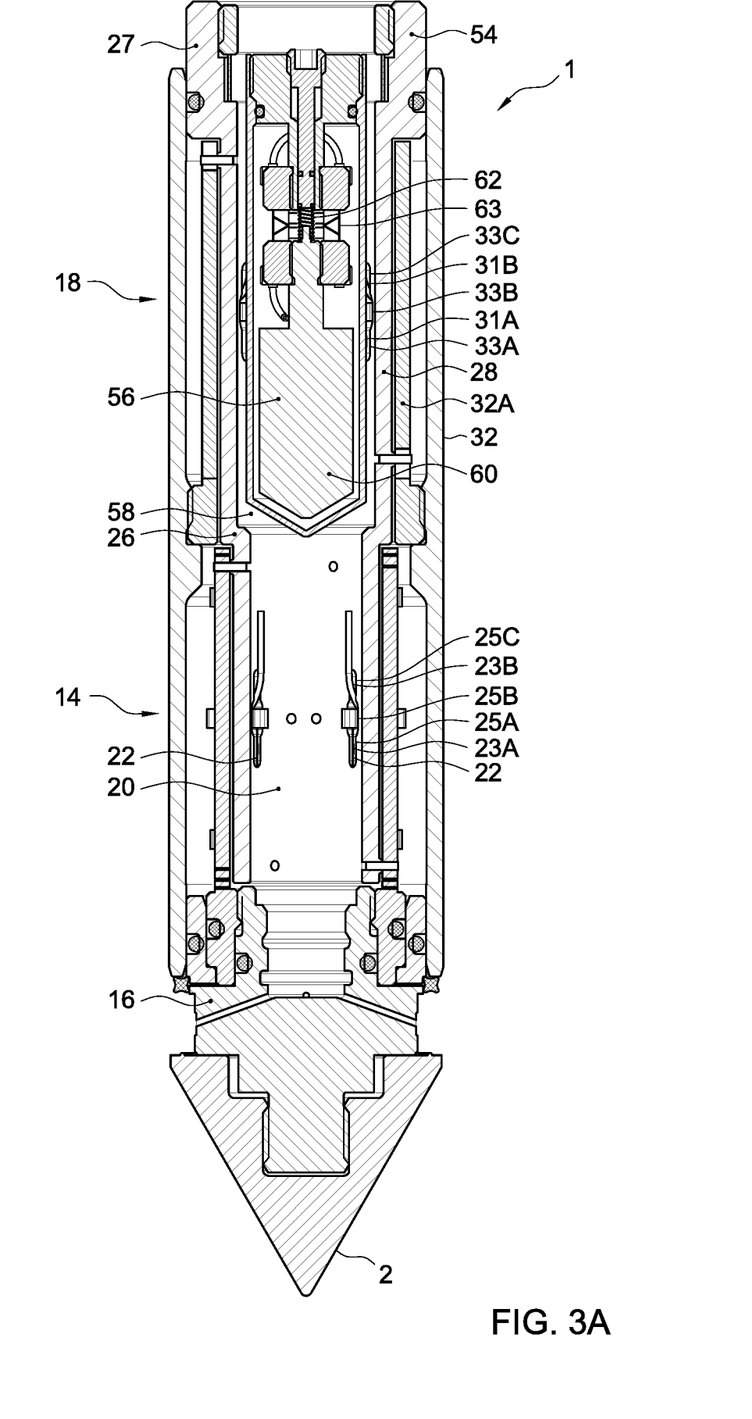
FIGS. 3A and 3B show schematic representations of an example of a cone penetrometer.

FIG. 3A shows a schematic representation of an example of a cone penetrometer 1. In this example in a first section 14, cone resistance measurement can be performed. The cone tip 2 is attached to a cone tip attachment unit 16.

In the first section 14 three first optic fiber portions 22 are provided, each provided with two Fiber Bragg Gratings 23A (FBG 1) and 23B (FBG 2). Here the two Fiber Bragg Gratings 23A, 23B have equal fiber length and stiffness. The three fiber portions 22 are radially distributed with 120 degree separations. By performing strain measurements at three locations radially distributed, effects of unequal loads at the tip and resulting bends can be corrected in the measurements. A cover protects the fiber portions 22 from mechanical damage. The three fiber portions 22 span the flexible section 20 to measure the length change of the deformable region.

Figure 3B:
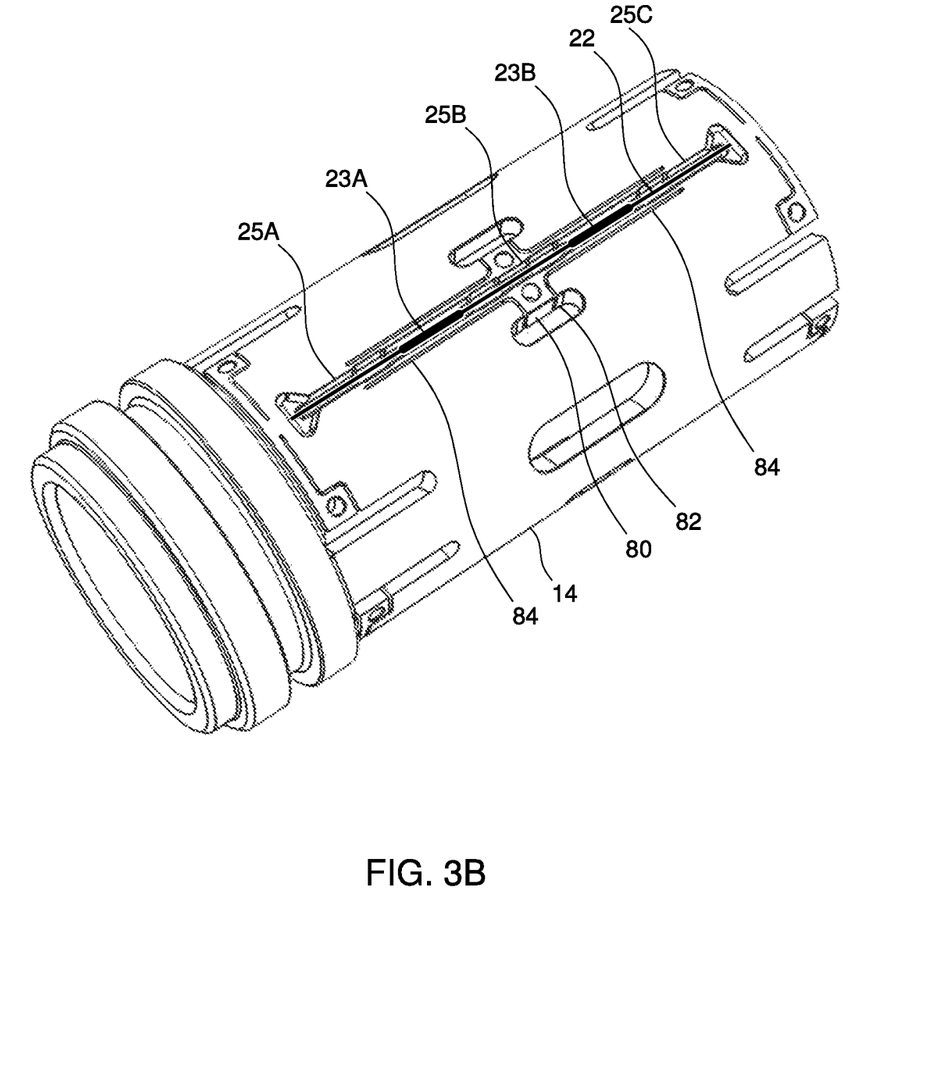

In this example, each fiber portion 22 is attached to the first section 14 at two outer attachments 25A, 25C, see FIG. 3B. Each fiber portion 22 is further attached to the cone tip 2, here via a cone sleeve 16A, at a center attachment 25B. The center attachment 25B is positioned between the two outer attachments 25A, 25C. The first Fiber Bragg Grating 23A is positioned between the first outer attachment 25A and the center attachment 25B. The second Fiber Bragg Grating 23B is positioned between the second outer attachment 25C and the center attachment 25B. In this example, the center attachment 25B is arranged to have limited travel relative to the outer attachments 25A, 25C. Here the center attachment 25B is attached to a shoe 80. Here the shoe 80 is movable in a recess 82 in the first section 14. Here the shoe 80 is connected to the first section 14 via resilient elements 84. Here the shoe 80 is unitary with the first section 14. Here the resilient elements 84 are formed by narrow members of the first section 14.

In this example, the first Fiber Bragg Grating 23A is arranged in series with the second Fiber Bragg Grating 23B. The first and second Fiber Bragg Gratings 23A, 23B form part of a single first fiber optic portion 22. A force exerted to the cone tip 2 will cause the center attachment 25B to be moved towards the first outer attachment 25A or the second outer attachment 25C. Hence, due to this force the first Fiber Bragg Grating 23A is extended and the second Fiber Bragg Grating 23B is shortened, or vice versa. As a result, the center frequency of the first Fiber Bragg Grating 23A goes up and the center frequency of the second Fiber Bragg Grating 23B goes down (see FIG. 4A), or vice versa. When the first section 14 is subject to changing temperatures, the first section may thermally expand or contract. Hence, the first outer attachment 25A and the second outer attachment 25C will both move outwardly or inwardly, respectively, with respect to the center attachment 25B. As a result, the center frequencies of the first and second Fiber Bragg Gratings 23A, 23B will both go up (see FIG. 4B) or down. Hence, the use of the first and second Fiber Bragg Gratings 23A, 23B allows to discern thermal expansion/extraction from forces exerted to the cone. Also in case of a combination of force exerted to the cone and thermal expansion/contraction, the measurement component due to thermal expansion/contraction can be determined. This allows for accurate measurements. This also allows for removing a thermal component from measurement results. Similarly, this allows for compensation of deformation of the cone body 54, such as compression or elongation, wherein the distance between the first outer attachment 25A and the second outer attachment 25C changes.

In a second section 18, sleeve friction measurement can be performed. A cover 32 is connected to the second section 18 and acts as a sleeve to provide the sleeve friction.

In the second section 18 three second optic fiber portions 30 are provided, each provided with two Fiber Bragg Gratings 31A and 31B. Here the two Fiber Bragg Gratings 31A, 31B have equal fiber length and stiffness. The three fiber portions 30 are radially distributed with 120 degree separations. By performing strain measurements at three locations radially distributed, effects of unequal loads at the tip and sleeve resulting bends can be corrected in the measurements. The cover 32 protects the fiber portions 30 from mechanical damage. The three fiber portions 30 span the flexible section 28 to measure the length change of the deformable region.

In this example, each fiber portion 30 is attached to the second section 18 at two outer attachments 33A, 33C. Each fiber portion 30 is further attached to the cover 32, here via a cover sleeve 32A, at a center attachment 33B. The center attachment 33B is positioned between the two outer attachments 33A, 33C. The first Fiber Bragg Grating 31A is positioned between the first outer attachment 31A and the center attachment 33B. The second Fiber Bragg Grating 31B is positioned between the second outer attachment 33C and the center attachment 33B. In this example, the center attachment 33B is arranged to have limited travel relative to the outer attachments 33A, 33C. Here the center attachment 33B is attached to a shoe 86. Here the shoe 86 is movable in a recess 88 in the second section 18. Here the shoe 86 is connected to the second section 18 via resilient elements 90. Here the shoe 86 is unitary with the second section 18. Here the resilient elements are formed by narrow members of the second section 18.

In this example, the first Fiber Bragg Grating 31A is arranged in series with the second Fiber Bragg Grating 31B. The first and second Fiber Bragg Gratings 31A, 31B form part of a single second fiber optic portion 30. A force exerted to the cover 32 will cause the center attachment 33B to be moved towards the first outer attachment 33A or the second outer attachment 33C. Hence, due to this force the first Fiber Bragg Grating 31A is extended and the second Fiber Bragg Grating 31B is shortened, or vice versa. As a result, the center frequency of the first Fiber Bragg Grating 31A goes up and the center frequency of the second Fiber Bragg Grating 31B goes down, or vice versa. When the second section 18 is subject to changing temperatures, the second section may thermally expand or contract. Hence, the first outer attachment 33A and the second outer attachment 33C will both move outwardly or inwardly, respectively, with respect to the center attachment 33B. As a result, the center frequencies of the first and second Fiber Bragg Gratings 31A, 31B will both go up or down. Hence, The use of the first and second Fiber Bragg Gratings 31A, 31B allows to discern thermal expansion/extraction from forces exerted to the cone. Also in case of a combination of force exerted to the cone and thermal expansion/contraction, the measurement component due to thermal expansion/contraction can be determined. This allows for accurate measurements. This also allows for removing a thermal component from measurement results.

Similarly as described with respect to FIGS. 2A and 2B, each of the fiber portions 22 in the first section 14 can be aligned with a corresponding fiber portion 30 in the second section 18. Each fiber portion 22 and the corresponding aligned fiber portion 30 can be part of a single optic fiber. The FBGs 23A, 23B of the fiber portion 22 can be tuned to a different wavelength than the FBGs 31A, 31B of the fiber portion 30. Thus FBGs of the first section and the second section can be chained onto one fiber and recorded simultaneously.

Figure 5:
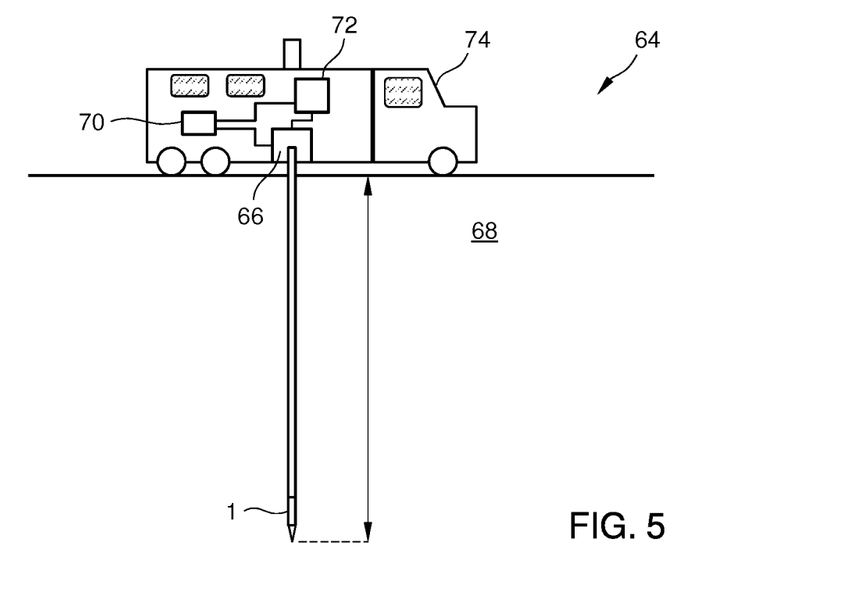
FIG. 5 shows a schematic representation of a probing system.

FIG. 5 shows a schematic representation of a probing system 64. The probing system includes a probe 1, e.g. as described with respect to FIGS. 1, 2A and 2B, or 3A and 3B. The probing system 64 further includes a drive unit 66 arranged for driving the probe 1 into the soil 68. Further, the probing system 64 includes a data acquisition system 70 arranged for sampling measurement signals from the probe 1. Here the data acquisition system includes a fiber optic interrogator arranged for carrying out interrogation of the one or more optical fiber sensors of the probe as described above. The probing system in this example includes a control unit 72. The control unit 72 is arranged for controlling the probe 1, the drive unit 66, and the data acquisition system 70. In this example, the probing system 64 is part of a probing vehicle 74.

The probe 2, or the probing system 64, can be used as follows. The probe 1 is pushed into a soil 68, e.g. by means of the drive unit 66. During pushing at least one of a cone resistance, sleeve friction, pore water pressure or inclination is determined as described above. The measurement results are representative for the soil.

Herein, the invention is described with reference to specific examples of embodiments of the invention. It will, however, be evident that various modifications and changes may be made therein, without departing from the essence of the invention. For the purpose of clarity and a concise description features are described herein as part of the same or separate embodiments, however, alternative embodiments having combinations of all or some of the features described in these separate embodiments are also envisaged.

Figure 4A:
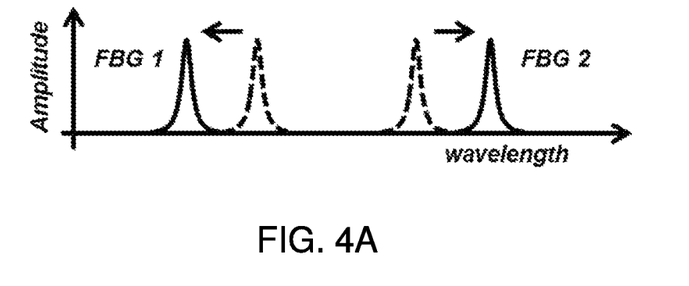
FIGS. 4A and 4B show schematic representations of FBG signals.
Figure 4B:
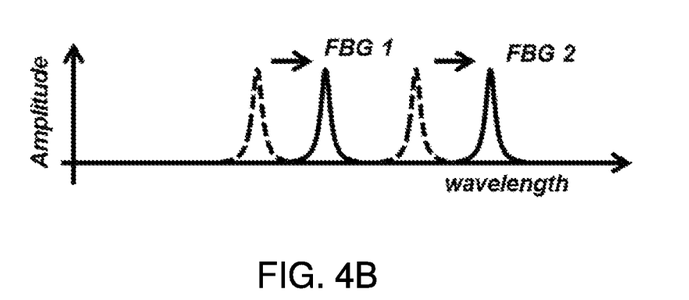

In the example of FIGS. 4A and 4B the two FGBs of a pair are tuned to different frequencies. It will be appreciated that it is also possible that the FBGs of a pair are tuned to the same frequency, i.e. having overlapping frequencies. In that case movement of the center attachment relative to the first and second outer attachments will cause a split in the frequencies, while movement of the first and second outer attachments relative to each other will cause the overlapping frequencies to move in unison.

While all of the FBGs can be placed on one fiber, inside the cone, for manufacturing and assembly practicality it is envisioned that they could be split to several fibers. This is feasible to accomplish in the cone body, in a fan-out type configuration, while maintaining only one fiber to connect to the outside.

Additionally, regarding data acquisition rates, while the interrogator can be operated at 1 kHz to record all the sensors, it can be that recordings up to 10 Hz are sufficient. As such, an averaging factor of 100 can be implemented to provide better signal to noise for all of the sensors.

However, other modifications, variations, and alternatives are also possible. The specifications, drawings and examples are, accordingly, to be regarded in an illustrative sense rather than in a restrictive sense.

For the purpose of clarity and a concise description features are described herein as part of the same or separate embodiments, however, it will be appreciated that the scope of the invention may include embodiments having combinations of all or some of the features described.

In the claims, any reference signs placed between parentheses shall not be construed as limiting the claim. The word 'comprising' does not exclude the presence of other features or steps than those listed in a claim. Furthermore, the words 'a' and 'an' shall not be construed as limited to 'only one', but instead are used to mean 'at least one', and do not exclude a plurality. The mere fact that certain measures are recited in mutually different claims does not indicate that a combination of these measures cannot be used to an advantage.

The invention claimed is:

1. A probe configured to measure properties of soil, comprising:
   a probe body including a cone tip configured to penetrate a soil; and
   at least one fiber optical sensor including a pair of Fiber Bragg Gratings (FBG) with a center attachment between a first FBG of the pair and a second FBG of the pair, the sensor configured to measure at least one of a cone resistance, sleeve friction, pore water pressure or inclination of the soil,
   wherein in response to a force exerted on the cone tip, the center attachment moves towards an outer attachment, the first FBG is extended, the second FBG is shortened and the pair have an oppose sign, and
   in a response to a temperature change the pair have a same sign.

2. The probe according to claim 1, wherein the at least one fiber optical sensor is configured to determine a force on an external surface of the probe.

3. The probe according to claim 1, wherein the probe body includes a first measurement section and three optic fiber portions, extending along the first measurement section in an axial direction of the probe body, for measuring cone resistance.

4. The probe according to claim 1, wherein the probe body includes a second measurement section and at least one fiber optic portion extending along the second measurement section in an axial direction of the probe body and configured to measure sleeve friction.

5. The probe according to claim 1, wherein a first optic fiber portion of a first measurement section aligns with a second optic fiber portion of a second measure section.

6. The probe according to claim 1, further comprising:
   a pore pressure sensor including an optic fiber portion extending between a displaceable diaphragm and a point fixed on the probe body in a closed chamber at a reference pressure.

7. The probe according to claim 1, further comprising:
   a temperature sensor including an optic fiber portion extending between two mounts free from mechanical strain.

8. The probe according to claim 1, further comprising a temperature reference sensor including an optic fiber portion.

9. The probe according to claim 1, wherein the at least one optical fiber sensor includes an optic fiber portion anchored by anchors wherein the anchors have a thermal expansion arranged to counteract a thermal expansion of the probe body between anchoring points of the optic fiber portion.

10. The probe according to claim 1, wherein the probe body includes a first measurement section and at least one first fiber optic portion extending along the first measurement section in an axial direction of the probe body, for measuring cone resistance.

11. The probe according to claim 10, wherein the first measurement section is a flexible section.

12. The probe according to claim 1, further comprising:
    an inclination sensor including a suspended mass pivotally connected to the probe body, and at least three optic fiber portions extending between the suspended mass and the probe body.

13. The probe according to claim 12, wherein the suspended mass is included in a chamber filled with a liquid.

14. The probe according to claim 1, wherein the pair of Fiber Bragg Gratings (FBG) arranged such that a force simultaneously causes an increase of tension of the first FBG of the pair and a decrease of tension of the second FBG of the pair.

15. The probe according to claim 14, further comprising: a sleeve for transferring a force from an external surface of the probe body onto the first and second FBG of the pair.

16. The probe according to claim 15, wherein the sleeve is connected to a single fiber optic portion between the first and second FBGs of the pair.

17. The probe according to claim 16, wherein the single fiber optic portion is connected to the probe body at attachments such that the first and second FBGs of the pair are positioned between the attachments.

18. A probing system including:
    a probe including a probe body and a cone tip;
    a drive unit configured to drive the probe into a soil;
    at least one fiber optical sensor including a pair of Fiber Bragg Gratings (FBG) with a center attachment between a first FBG of the pair and a second FBG of the pair, the sensor configured to measure at least one of a cone resistance, sleeve friction, pore water pressure or inclination of the soil; and
    a data acquisition system configured to sample measurement signals from the probe, including a fiber optic interrogator configured to interrogate the at least one optical fiber sensors of the probe,
    wherein in response to a force exerted on the cone tip, the center attachment moves towards an outer attachment, the first FBG is extended, the second FBG is shortened and the pair have an oppose sign, and
    in a response to a temperature change the pair have a same sign.

19. A method for determining soil properties, comprising:
    pushing a probe into a soil, the probe comprising a probe body including a cone tip and at least one fiber optical sensor including a pair of Fiber Bragg Gratings (FBG) with a center attachment between a first FBG of the pair and a second FBG of the pair, wherein in response to a force exerted on the cone tip, the center attachment moves towards an outer attachment, the first FBG is extended, the second FBG is shortened and the pair have an oppose sign, and in a response to a temperature change the pair have a same sign;

measuring, via the at least one fiber optical sensor, at least one of a cone resistance, sleeve friction, pore water pressure or inclination, determining at least one of a cone resistance, sleeve friction, pore water pressure or inclination based on the measurements.

\* \* \* \* \*